(12) United States Patent
Asiri et al.

(10) Patent No.: US 10,317,356 B2
(45) Date of Patent: Jun. 11, 2019

(54) COPPER(II) OXIDE AND CELLULOSE ACETATE COMPOSITE RESISTANCE-BASED HUMIDITY SENSOR

(71) Applicant: King Abdulaziz University, Jeddah (SA)

(72) Inventors: Abdullah Mohamed Asiri, Jeddah (SA); Muhammad Tariq Saeed Chani, Jeddah (SA)

(73) Assignee: King Abdulaziz University, Jeddah (SA)

( * ) Notice: Subject to any disclaimer, the term of this patent is extended or adjusted under 35 U.S.C. 154(b) by 288 days.

(21) Appl. No.: 15/456,623

(22) Filed: Mar. 13, 2017

(65) Prior Publication Data
US 2018/0259471 A1    Sep. 13, 2018

(51) Int. Cl.
*G01N 27/04* (2006.01)
*G01N 27/12* (2006.01)

(52) U.S. Cl.
CPC ......... *G01N 27/126* (2013.01); *G01N 27/121* (2013.01)

(58) Field of Classification Search
CPC .................................................... G01N 27/121
See application file for complete search history.

(56) References Cited

U.S. PATENT DOCUMENTS

| | | | |
|---|---|---|---|
| 4,481,813 A | 11/1984 | Tanei et al. | |
| 8,707,781 B2 | 4/2014 | Humbert et al. | |
| 2010/0307238 A1 | 12/2010 | Van Popta et al. | |
| 2011/0146400 A1* | 6/2011 | Humbert | G01N 27/223 73/335.04 |

FOREIGN PATENT DOCUMENTS

| | | |
|---|---|---|
| EP | 0 779 773 A1 | 6/1997 |
| JP | 4-238261 A | 8/1992 |

OTHER PUBLICATIONS

Mohammad Mansoob Khan, et al., "Metal oxides as photocatalysts", Journal of Saudi Chemical Society, vol. 19, Issue 5, Sep. 2015, pp. 462-464.
(Continued)

*Primary Examiner* — Son T Le
*Assistant Examiner* — Alex T Devito
(74) *Attorney, Agent, or Firm* — Oblon, McClelland, Maier & Neustadt, L.L.P.

(57) ABSTRACT

A resistance-based humidity sensor including a moisture sensitive composite comprising a cellulose acetate and copper(II) oxide and a first electrode and a second electrode each in direct contact with the composite. Each electrode is connected to a circuit which can correlate a resistance of the composite to a measurement of a relative humidity. The method by which the sensor may measure a relative humidity in an environment includes applying a frequency through the first electrode, across the moisture sensitive composite, and through a second electrode to measure a change in the frequency that correlates to a resistance of the moisture sensitive composite and correlates to the relative humidity of the environment. A method of producing a resistance-based humidity sensor in the form of a film or in the form of a cell.

20 Claims, 10 Drawing Sheets

(56) References Cited

OTHER PUBLICATIONS

Zubair Ahmad, et al., "Bi-Layer Capacitive Type Light and Humidity Sensors", Journal of Ovonic Research, vol. 4, No. 5, Oct. 2008, pp. 91-95.
H.T. Hsueh, et al., "CuO nanowire-based humidity sensors prepared on glass substrate", Sensors and Actuators B: Chemical, vol. 156, 2011, pp. 906-911.
Vincent Ducéré, et al., "A capacitive humidity sensor using cross-linked cellulose acetate butyrate", Sensors and Actuators B, vol. 106, 2005, pp. 331-334.
X.H. Huang, et al., "Porous ZnO nanosheets grown on copper substrates as anodes for lithium ion batteries", Electrochimica ACTA, vol. 56, 2011, pp. 4960-4965.
Yang Liu, et al., "Facile fabrication of CuO nanosheets on Cu substrate as anode materials for electrochemical energy storage", Journal of Alloys and Compounds, vol. 586, 2014, pp. 208-215.
Suresha K. Mahadeva, et al., "Flexible humidity and temperature sensor based on cellulose-polypyrrole nanocomposite", Sensors and Actuators A: Physical, vol. 165, 2011, pp. 194-199.
M. Tariq Saeed, et al., "Organic Cu/cellulose/ PEPC/Cu humidity sensor", Optoelectronics and Advanced Materials—Rapid Communications, vol. 4, No. 6, Jun. 2010, pp. 888-892.
Qi Qi, et al., "Humidity sensing properties of KCI-doped Cu—Zn/CuO—ZnO nanoparticles", Sensors and Actuators B: Chemical, vol. 137, 2009, pp. 21-26.

\* cited by examiner

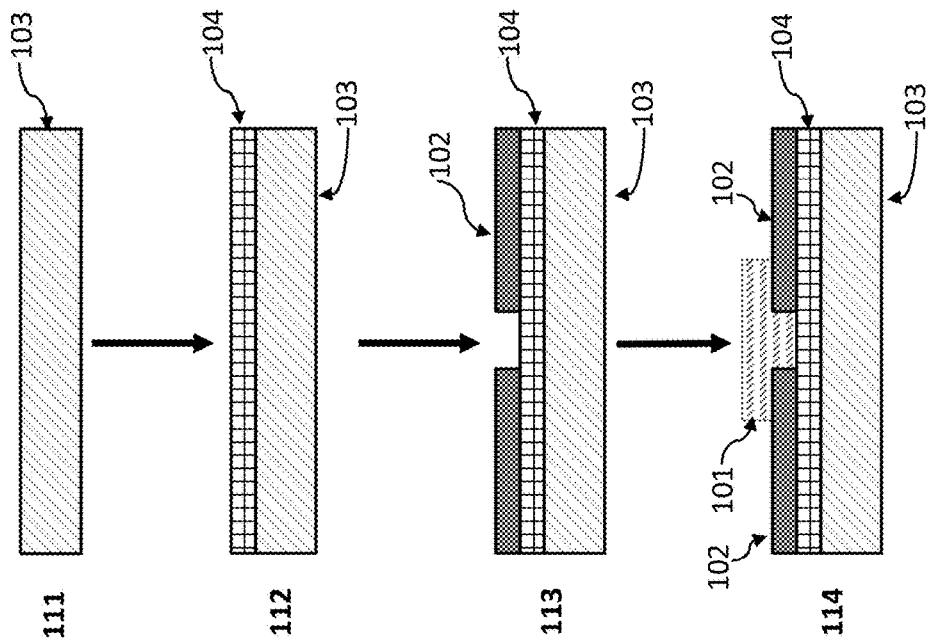
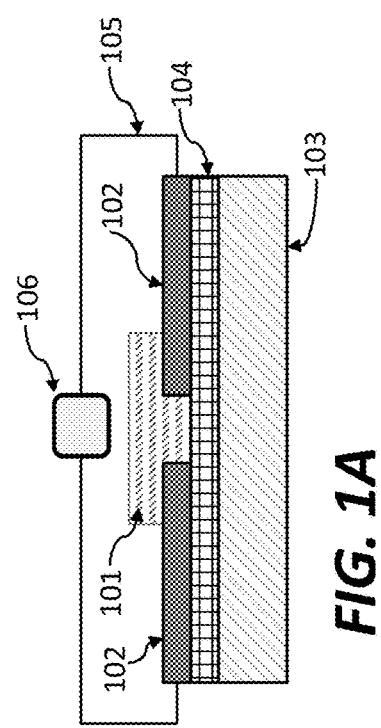
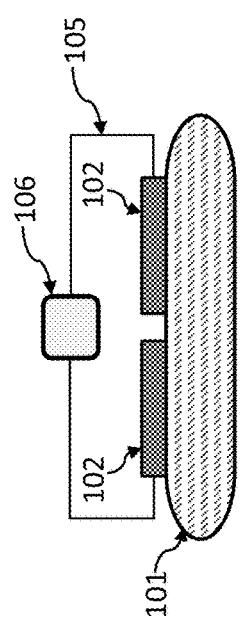
FIG. 1A
FIG. 1B
FIG. 1C

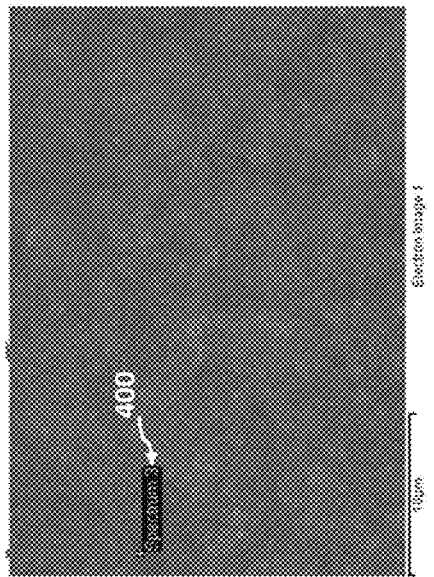
FIG. 4A
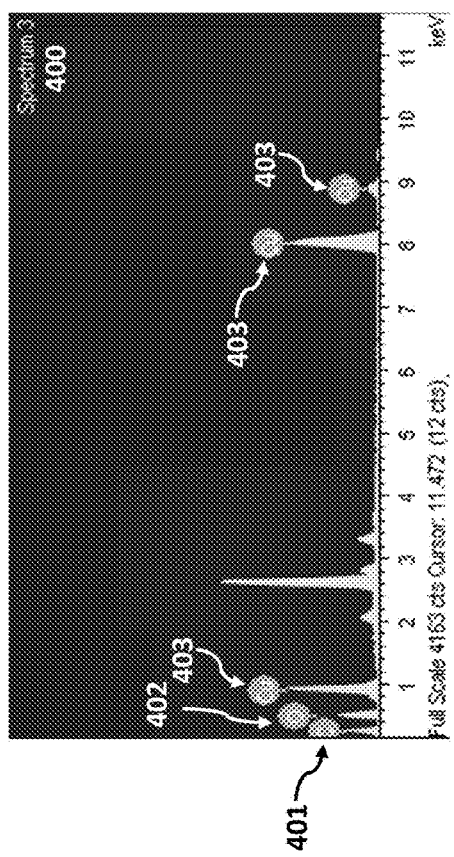
FIG. 4B
FIG. 4C

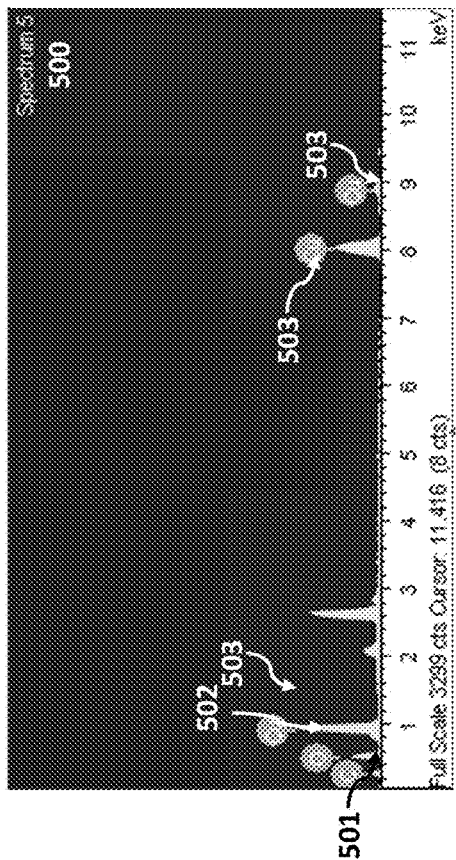
FIG. 5B
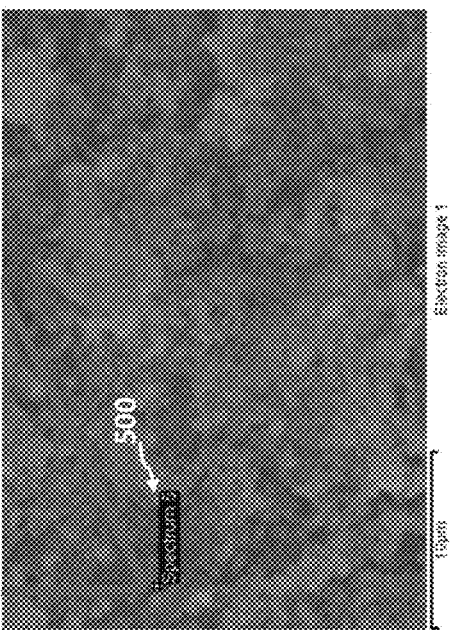
FIG. 5A
FIG. 5C

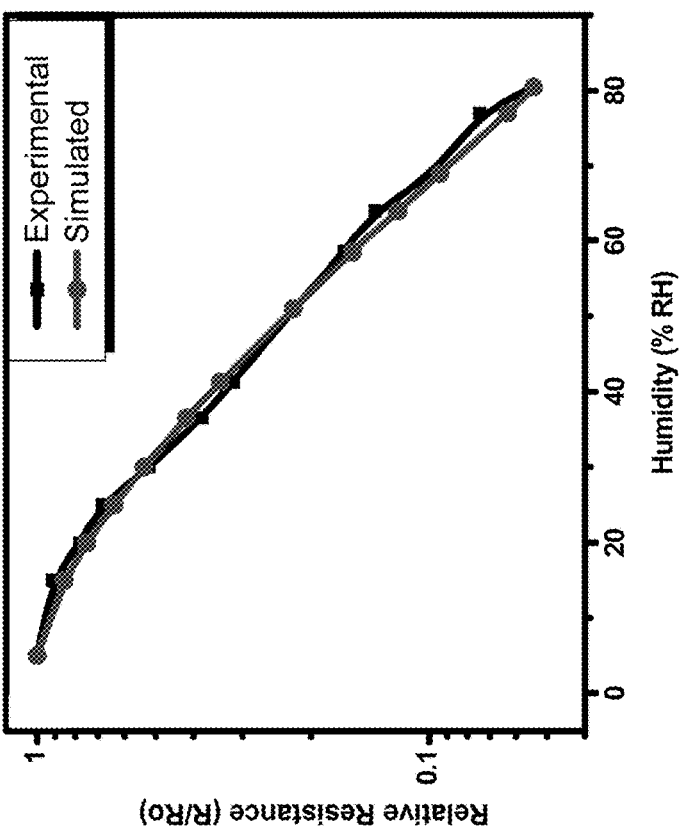
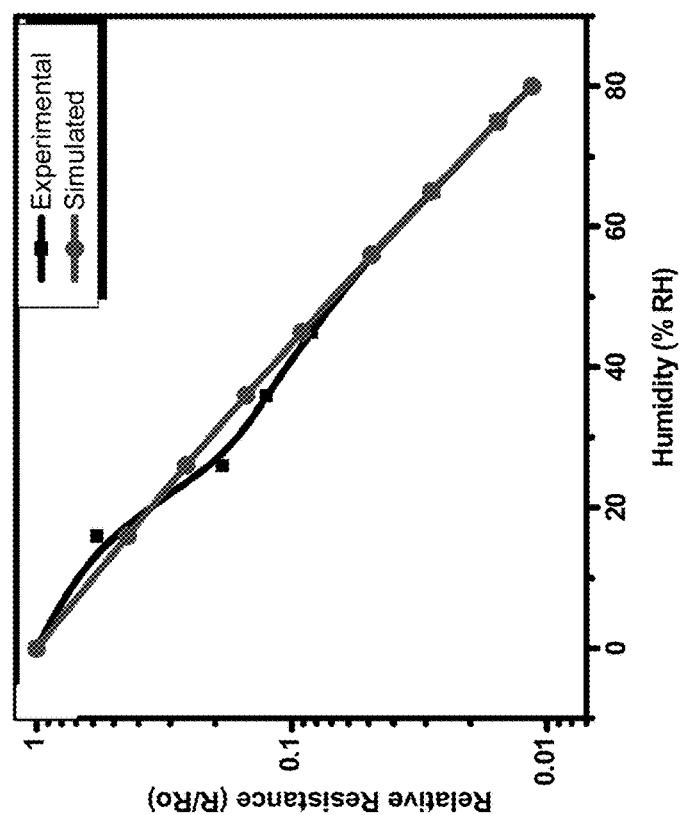
FIG.10A
FIG.10B

COPPER(II) OXIDE AND CELLULOSE ACETATE COMPOSITE RESISTANCE-BASED HUMIDITY SENSOR

BACKGROUND OF THE INVENTION

Technical Field

The present invention relates to an organic electronic sensor employing a composite for sensing relative humidity.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

In sensor systems, performance of the sensor is highly dependent on the materials which make up the sensor. The materials commonly employed for humidity sensors include ceramics, metals, poly-electrolytes, polymers, low molecular weight organic materials, porous organic/inorganic materials, nano-materials and nano-composites. Although inorganic materials have good physical and chemical stability, they exhibit drift, low sensitivity and poor reversibility; while organic materials are cheap, light weight, flexible, highly sensitive and easy to fabricate. These properties make the organic materials very promising for use as sensing materials in humidity sensors. Of many potential organic materials, polymers which may be prepared from a variety of compositions and retain a variety of functional groups, such as aromatics, ammonium ions, sulfonic acids, and carboxylic acids, show good humidity sensing properties.

In a conventional humidity sensor made of metal oxide, a metal oxide is coated onto the surfaces of a substrate to form a humidity sensing film. The sensor utilizes a phenomenon in which the electrical resistive value of the humidity sensing film varies due to a variation in humidity. The humidity sensor made of metal oxide has physically, chemically and thermally stable properties, but has a relatively high resistivity. Since a change of a resistance resulting from a change in humidity is relatively small, it is difficult to accurately detect a change of an electrical resistance.

Humidity sensors can be classified as resistive, capacitive, impedance, colorimetric and surface acoustic wave sensors. Organic materials for resistive type sensors are conjugated polymers and poly electrolytes, while for capacitive type sensors hydrophobic polymers are used. Cellulose acetate is a hydrophobic polymer with fairly hygroscopic nature to adsorb water molecule and it has been used in different forms by various researchers to develop the humidity sensors. The sensors based on hydrophobic materials have linear response and exhibit a large hysteresis. To overcome the large hysteresis, the modification of polymeric materials is carried out by incorporation of additives. Ducere et al. fabricated and investigated a sandwich type capacitive humidity sensor based on cross-linked cellulose acetate butyrate. See Ducéré, Vincent, Alain Bernès, and Colette Lacabanne. "A capacitive humidity sensor using cross-linked cellulose acetate butyrate." Sensors and Actuators B: Chemical 106.1 (2005): 331-334, incorporated by reference herein in its entirety. It was reported that the sensor operated efficiently between −40° C. to 120° C. for the measurement of 0% to 100% RH. Saeed et al. reported a surface type humidity sensor based on composite of cellulose-poly-N-epoxypropylcarbazole (PEPC). See Saeed, M., et al. "Organic Cu/cellulose/PEPC/Cu humidity sensor." Optoelectronics and Advanced Materials-Rapid Communications 4.6 (2010): 888-892, incorporated herein by reference in its entirety. The results reveal that by changing humidity from 45% to 89% RH, the capacitance of the sensor increased 21 times, while the resistance decreases by 1740 times. Ahmad et al. fabricated a capacitive type bi-layer sensor for light and humidity sensing. See Ahmad, Zubair, Muhammad H. Sayyad, and Khasan S. Karimov. "Bi-layer capacitive type light and humidity sensors." J Ovonic Research 4 (2008): 91, incorporated herein by reference in its entirety. It was reported that the cellulose-copper phthalocyanine composite based sensor is more sensitive to humidity than only cellulose based sensor. Mahadeva et al. fabricated flexible sensors based on cellulose-polypyrrole nano-composite for humidity and temperature measurement. It was reported that the sensors showed good response, reversibility, and linearity. See Mahadeva, Suresha K., Sungryul Yun, and Jaehwan Kim. "Flexible humidity and temperature sensor based on cellulose-polypyrrole nanocomposite." Sensors and Actuators A: Physical 165.2 (2011): 194-199, incorporated herein by reference in its entirety.

Copper(II) oxide (CuO) is a p-type semiconductor having an energy band gap of 1.2 eV. It has applications in sensors, solar cells, catalysis, field emission and other electronic devices. CuO can be used in fabricating a variety of sensors such as humidity, temperature, chemical and gas sensors.

Copper(II) oxide nanowires grown on a glass substrates were used for humidity sensing by Hsueh et al. See Hsueh, H. T., et al. "CuO nanowire-based humidity sensors prepared on glass substrate." Sensors and Actuators B: Chemical 156.2 (2011): 906-911, incorporated herein by reference in its entirety. It was concluded that the humidity sensing mechanism of the nanowires was based on resistance change and that the short nanowires showed less sensitivity as compared to long nanowires. The 20% to 90%/a change in humidity caused an increase in resistance from 0.55 MΩ to 0.62 MΩ, which was attributed to p-type semiconducting nature of copper(II) oxide. The KCl-doped and undoped Cu—Zn/CuO—ZnO nanoparticles based humidity sensors were fabricated on to the Ag—Pd integrated electrodes (5 pairs) by Qi et al. See Qi, Qi, et al. "Humidity sensing properties of KCl-doped Cu—Zn/CuO—ZnO nanoparticles." Sensors and Actuators B: Chemical 137.1 (2009): 21-26, incorporated herein by reference in its entirety. The results showed that the sensors made of doped material have greater detection limit with more linear response as compared to the sensors made of un-doped material. The rise in humidity from 11% to 95% causes a decrease in the impedance of doped sensors by four orders of magnitude.

Contingent on the design of synthesis, the nanomaterials can be formed in different sizes, morphologies and compositions. Depending upon the morphology the nanomaterials are categorized as nanopowders, nanorods, nanotubes, nanobats, nanosheets and nanoflowers. Being widely used semiconducting materials the CuO and ZnO are studied in different forms; particularly the nanosheets are used for a variety of applications such as sensing, supercapacitors, solar cells, anode for lithium ion batteries and metal ion uptake. The CuO and ZnO nanosheets were fabricated on Cu substrate by Liu et al. and Huang et al., respectively and then applied as an anode in lithium-ion batteries. See Liu, Yang, et al. "Facile fabrication of CuO nanosheets on Cu substrate as anode materials for electrochemical energy storage." Journal of Alloys and Compounds 586 (2014): 208-215 and Huang, X. H., et al. "Porous ZnO nanosheets grown on copper substrates as anodes for lithium ion batteries." Electrochimica Acta 56.14 (2011): 4960-4965, each incorporated herein by reference in their entirety. The CuO nanosheets anode showed the discharge capacity of 442 mAhg$^{-1}$ after 40 cycles at 200 mAg$^{-1}$ (current density), while the discharge capacity of ZnO was 400 mAhg$^{-1}$ after 100 cycles at 500 mAg$^{-1}$ (current density). For the humidity sensing of the CuO nanosheets, sensitivity of pure CuO nanosheets and CuO-silicone adhesive composite was found −4.88% per % RH and −2.9% per % RH, respectively.

The existing commercial humidity sensors based on high density inorganic materials like alumina, electrolytic metal oxides, and ceramics have the disadvantages of lower stability, low-sensitivity, slow response, large hysteresis and complex fabrication. However, because of their extensive utility in a variety of industrial applications, such as monitoring equipment operations and environmental monitoring, there is a need to continuously develop humidity sensors that have low density, lower cost, simplified fabrication, linear response, high sensitivity, fast response, and recovery, small hysteresis, low power consumption and excellent chemical and physical stability. These properties may make a sensor very attractive for commercialization.

In view of the forgoing, one objective of the present invention is to employ cupric oxide or copper(II) oxide (CuO) with cellulose acetate (CA) as a composite for a humidity sensor.

BRIEF SUMMARY OF THE INVENTION

According to a first aspect, a resistance-based humidity sensor having a moisture sensitive composite comprising a cellulose acetate and copper(II) oxide and a first electrode and a second electrode each in direct contact with the composite, wherein the first electrode and the second electrode are separated by the composite. Each electrode is connected to a circuit which can correlate a resistance of the composite to a measurement of a relative humidity.

In some embodiments of the resistance-based humidity sensor, a ratio of cellulose acetate to copper(II) oxide by weight is in a range of 1:4 to 4:1.

In some embodiments of the resistance-based humidity sensor, the first and second electrodes are silver, gold, aluminum, or a combination thereof.

In some embodiments of the resistance-based humidity sensor, the resistance-based humidity sensor further includes an inert substrate, wherein the moisture sensitive composite is on the inert substrate.

In some embodiments of the resistance-based humidity sensor, the resistance-based humidity sensor further includes an adhesive layer between at least a portion of the moisture sensitive composite and the surface of the inert substrate.

In some embodiments of the resistance-based humidity sensor, the inert substrate is nonporous.

In some embodiments of the resistance-based humidity sensor, the composite is in the form of a film having a thickness in the range of 10 micron to 50 micron.

In some embodiments of the resistance-based humidity sensor, at an applied frequency in the range of 80 Hz to 120 Hz, the resistance-based humidity sensor has an initial average resistance in the range of 250 MΩ to 500 MΩ, and an average capacitance in the range of 10 pF to 20 pF, and the average change in resistance is in the range of 2 MΩ per 1% relative humidity to 5 MΩ per 1% relative humidity and an average change in capacitance in the range of 10 pF per 1% relative humidity to 25 pF per 1% relative humidity.

In some embodiments of the resistance-based humidity sensor, the composite is in the form of a cell having at least one dimension in the range of 2 mm to 10 mm.

In some embodiments of the resistance-based humidity sensor, at an applied frequency in the range of 80 Hz to 120 Hz, the resistance-base humidity sensor has an average resistance in the range of 15 MΩ to 40 MΩ, and the average change in resistance is in the range of 0.1 MΩ per 1% relative humidity to 1 MΩ per 1% relative humidity.

In some embodiments of the resistance-based humidity sensor, the sensor has a response time in the range of 8 seconds to 18 seconds and a recovery time in the range of 12 seconds to 22 seconds.

According to a second aspect, a method of measuring a relative humidity in an environment with the resistance-based humidity sensor, including applying a frequency through the first electrode, across the moisture sensitive composite, and through a second electrode to measure a change in the frequency that correlates to a measurement of a resistance of the moisture sensitive composite and correlates to the relative humidity of the environment.

According to a third aspect, a method of producing a resistance-based humidity sensor, including mixing a first mixture comprising copper(II) oxide and an alcohol with cellulose acetate to form a second mixture, attaching at least two electrodes to an inert substrate, such that the two electrodes are spaced apart by at least 30 microns, depositing the second mixture onto at least a portion of the inert substrate such that the mixture contacts at least a portion of each of the electrodes, and drying the second mixture.

In some embodiments of the method of producing the resistance-based humidity sensor, a ratio of cellulose acetate to copper(II) oxide by weight is in the range of 1:4 to 4:1.

In some embodiments of the method of producing the resistance-based humidity sensor, the electrodes are silver, gold, aluminum, or a combination thereof.

In some embodiments of the method of producing the resistance-based humidity sensor, the inert substrate is nonporous.

According to a fourth aspect, a method of producing a resistance-based humidity sensor, including mixing copper (II) oxide and cellulose acetate forming a mixture, molding the mixture into a cell and attaching at least two electrodes to the cell, spaced at a minimum of 30 micron, and drying the cell.

In some embodiments of the method of producing the resistance-based humidity sensor, a ratio of cellulose acetate to copper(II) oxide by weight is in the range of 1:4 to 4:1.

In some embodiments of the method of producing the resistance-based humidity sensor, the electrodes are silver, gold, aluminum, or a combination thereof.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIG. 1A is an exemplary schematic of a resistance-based sensor in a film configuration;

FIG. 1B is an exemplary schematic of a resistance-based sensor in a cell configuration;

FIG. 1C is an exemplary schematic flow chart of the sequence to produce the resistance-based sensor in the film configuration;

FIG. 4A is a FESEM image of the surface of the resistance-based sensor in the film configuration employed for EDS analysis of CA-CuO composites;

FIG. 4B is a table of the values measured from an EDS analysis for the CA-CuO composite of the resistance-based sensor in the film configuration;

FIG. 4C is an EDS spectrum for the CA-CuO composite of the resistance-based sensor in the film configuration;

FIG. 5A is a is a FESEM image of the surface of the resistance-based sensor in the cell configuration employed for EDS analysis of CA-CuO composites;

FIG. 5B is a is a table of the values measured from an EDS analysis for the CA-CuO composite of the resistance-based sensor in the cell configuration;

FIG. 5C is a an EDS spectrum for the CA-CuO composite of the resistance-based sensor in the cell configuration;

FIG. 10A is an exemplary plot of a normalized experimental and normalized simulated resistance-humidity relationship for the CA-CuO composite resistance-based humidity sensor in the film configuration; and FIG. 10B is an exemplary plot of a normalized experiment and a normalized simulated resistance-humidity relationship for the CA-CuO composite resistance-based humidity sensor in the cell configuration.

DETAILED DESCRIPTION OF THE EMBODIMENTS

Figure 2B:
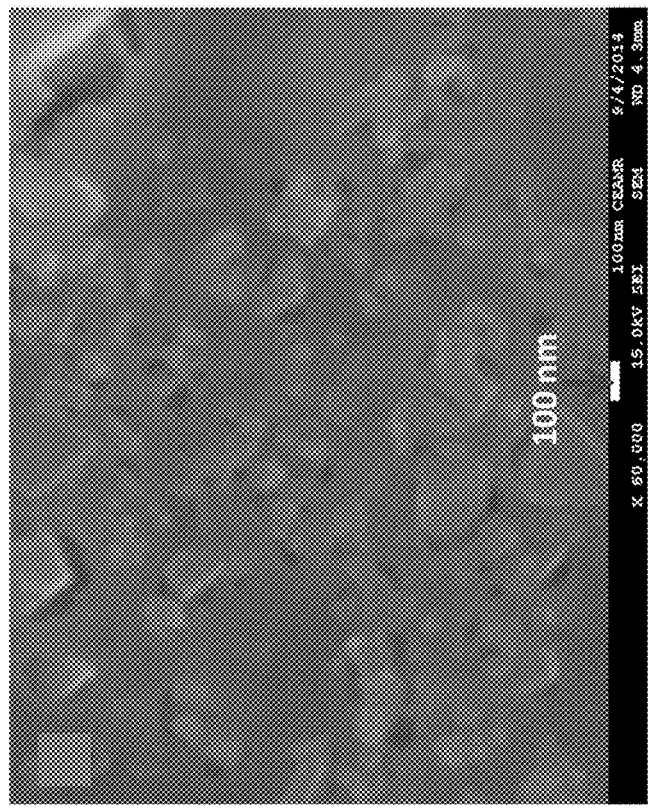
FIG. 2B is a FESEM image at 60000× of a surface of the resistance-based sensor in the film configuration.

Referring now to the drawings, wherein like reference numerals designate identical or corresponding parts throughout the several views.

An aspect of the present disclosure relates to a resistance-based humidity sensor having a moisture sensitive composite comprising a cellulose acetate and copper(II) oxide and a first electrode and a second electrode, separated by the composite. Each electrode may be connected to a circuit which can correlate a resistance of the composite to a measurement of a relative humidity. The moisture sensitive composite may exhibit different characteristics relative to the moisture content of the surrounding environment. The moisture in the environment may interact with the moisture sensitive composite such that the characteristics of the moisture sensitive composite, such as resistance, differ based on the moisture in the environment.

The moisture sensitive composite employs cellulose acetate, which is the acetate ester derivative of a plant derived polymer, cellulose, which may be extracted from green plants. The density of cellulose acetate may be in the range of 1 $g/cm^3$ to 2 $g/cm^3$ and 1.5 $g/cm^3$ to 1.75 $g/cm^3$. Cellulose acetate is able to absorb water from the air, unlike the transition-metal oxide, cupric oxide. The cupric oxide, or copper(II) oxide (CuO) is an p-type semiconductor having a narrow band gap energy (1.2-1.6 eV) and eccentric band structure, which is analogous to Mott insulator materials. Mott insulators are a class of materials that should conduct electricity under conventional band theories, but are insulators when measured at low temperatures. Because of cupric oxide's electronic, catalytic, and electrochemical properties and the versatility of nanostructures, cupric oxide has been used for the sensor of the present disclosure. A composite of cellulose acetate (CA) and cupric oxide (CuO) were employed in the fabrication of the humidity sensor described herein.

In some embodiments of the resistance-based humidity sensor, a ratio of cellulose acetate to copper(II) oxide by weight is in a range of 1:4 to 4:1, 2:3 to 3:2, or most preferably 2:1 to 1:1. In some embodiments, cellulose acetate may be substituted with cellulose acetate butyrate, cellulose acetate propionate, cellulose acetate phthalate, or cellulose triacetate. The average molecular weight range of the cellulose acetate or any substitutes of cellulose acetate may be 9,000 g/mol to 100,000 g/mol, 10,000 g/mol to 80,000 g/mol, 20,000 g/mol to 60,000 g/mol, or 30,000 g/mol to 40,000 g/mol. In some embodiments, the moisture sensitive composite may include any of the above listed substitutes of cellulose acetates in a weight percentage relative to the total weight of the composite of 0.25% to 50%, 5% to 40%, 10% to 30%, or 15% to 20%. In some embodiments, the moisture sensitive composite may include metal oxides, such as, but not limited to copper(II) oxide, nickel oxide, cobalt oxide, iron oxide ($Fe_2O_3$ or $Fe_3O_4$), zinc oxide, cadmium oxide, zirconium oxide, rubidium oxide, cerium oxide, barium oxide, manganese oxide, magnesium oxide, beryllium oxide, gallium oxide, lanthanum oxide, calcium oxide, geranium oxide, chromium oxide, or tin oxide, in a percentage relative to the total weight of the composite of 0.25% to 50%, 5% to 40%, 10% to 30%, or 15% to 20%. Titanium dioxide is not included in the moisture sensitive composite of the present disclosure. In some embodiments, the moisture sensitive composite consists of cellulose acetate and copper(II) oxide.

In some embodiments of the moisture sensitive composite, the cellulose acetate and the cupric oxide may form non-covalent electrostatic interactions between the copper and the carboxylic oxygens of the acetates on the cellulose, Van der Waals interactions between the oxygen of the cupric oxide and at least one of the acidic hydrogen atoms (α-hydrogen atoms) of the acetate on the cellulose or hydrogen bonding interactions between the oxygen of the cupric oxide and the equatorial hydroxyl groups on the cellulose in the cellulose acetate.

The moisture sensitive composite may be porous in some embodiments, and may have pores of an average pore diameter of about 0.01 nm to about 50 nm, about 0.1 nm to about 15 nm, about 0.5 nm to about 10 nm, about 1 nm to about 8 nm, about 2 nm to about 6 nm. The pores may be formed in a matrix of the moisture sensitive composite. The matrix comprises the cellulose acetate and particles of cellulose acetate and cupric oxide, described further herein.

FIG. 1A and FIG. 1B depict two exemplary schematics of the presently disclosed resistance-based humidity sensor. In FIG. 1A and FIG. 1B the moisture sensitive composite 101 is placed in contact with the electrodes 102. In some embodiments of the resistance-based humidity sensor, the sensor further includes an inert substrate 103. In some embodiments of the resistance-based humidity sensor, the inert substrate 103 is nonporous. The nonporous inert substrate may comprise glass, plastic, a combination thereof, or the like. In some embodiments, the inert substrate excludes alumina. The inert substrate is non-conductive and will not absorb moisture or retain moisture. Further, in some embodiments as depicted in FIG. 1A, the resistance-based humidity sensor includes the inert substrate 103 on which the moisture sensitive composite 101 is in direct contact with the electrodes 102 and an adhesive layer, when present, separates the electrodes and the composite from the inert substrate. FIG. 1C is an exemplary graphical representation of the sequence by which each part of the humidity sensor may be added to a substrate.

In some embodiments, the resistance-based humidity sensor further includes an adhesive layer 104 between at least a portion of the moisture sensitive composite and the surface of the inert substrate. In some embodiments the adhesive layer is in direct contact with the composite, the electrodes and the inert substrate. FIG. 1A depicts an exemplary embodiment in which the adhesive layer 104 is between the moisture sensitive composite 101 and the electrodes 102, and the inert substrate 103. In some embodiments, the portion of the moisture sensitive composite 101 surface area or the surface area of the inert substrate 103 which the adhesive layer 104 may contact may be 5% to 50% Y, 10% to 40%, 20% to 30%. The adhesive layer 104 is optional, wherein some embodiments of the resistance-based humidity sensor may have the inert substrate directly in contact with the electrodes and the moisture sensitive composite. In some embodiments, the electrodes may be integrated into the inert substrate and directly in contact with the composite. The adhesive layer, when included, may comprise an adhesive tape, a nitrocellulose adhesive, an acrylic adhesive, a cyanoacrylate adhesive, a pressure-sensitive adhesive (e.g polyurethane pressure sensitive adhesive, polyester pressure sensitive adhesive), a heat sensitive adhesive (e.g. thermoplastic polyolefin), or elastomeric adhesive (e.g. chloroprene or nitrile rubber). The adhesive layer may be a thickness of 100 nm to 9 mm, 500 nm to 8 mm, 1 micron to 7 mm, 10 micron to 6 mm, 100 micron to 5 mm, 1 mm to 4 mm, or 2 mm to 3 mm.

FIG. 1A depicts an embodiment of the resistance-based humidity sensor in which the composite is in the form of a film having a thickness in the range of 10 micron to 50 micron, 20 micron to 40 micron, or 25 micron to 30 micron, a length in the range of 2 mm to 15 mm, 5 mm to 10 mm, or 6 mm to 8 mm, and a width in the range of 2 mm to 15 mm, 5 mm to 10 mm, or 6 mm to 8 mm. FIG. 1B depicts an exemplary resistance-based humidity sensor in which the moisture sensitive composite 101 is formed into a three dimensional cell, which may be in shapes including, but not limited to cylindrical, cubic, or pellet. The cell differs from the film by the thickness measurement by at least 100 times. The cell may be a length of 2 mm to 10 mm or 4 mm to 7 mm and a thickness of 1 mm to 10 mm, 2 mm to 8 mm, or 4 mm to 6 mm. In some embodiments, such as that depicted in FIG. 1B, the resistance-based humidity sensor does not include the inert substrate, however the inert substrate may be included to provide a flat surface by which the sensor can be attached to a surface on a wall or a surface of industrial equipment. Further the adhesive layer may be included between the composite and the inert substrate to facilitate adhesion. In some embodiments of the resistance-based humidity sensor configured in the form of the cell, the electrodes may be spaced in the range of 2 mm to 10 mm apart, 3 mm to 9 mm apart, 4 mm to 8 mm apart, or 5 mm to 7 mm apart.

Figure 2A:
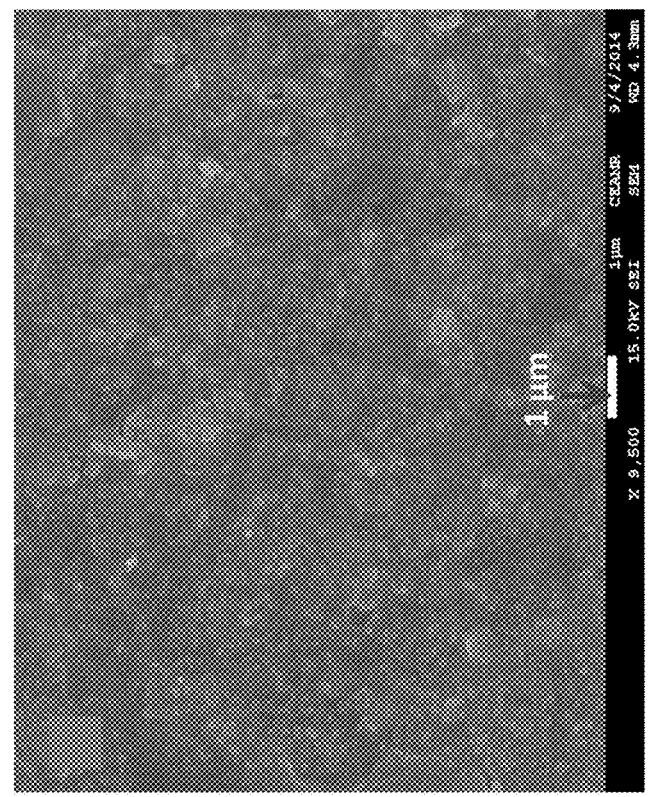
FIG. 2A is a FESEM image at 9500× of a surface of the resistance-based sensor in the film configuration.

Exemplary images of the composite in the film configuration, imaged at high magnification, are shown in FIG. 2A and FIG. 2B. FIG. 2A is an exemplary section of the composite in the film configuration at 9500× magnification and FIG. 2B is the same exemplary section of the composite in the film configuration at 60000× magnification. In the film configuration, the composite is relatively uniform, having a porosity of 0%-25%, 1%-15%, or 5%-10% relative to the whole surface area of the exemplary section and further, the pores are an average size of 75 nm to 700 nm, 100 nm to 600 nm, 150 nm to 550 nm, 200 nm to 500 nm, 250 nm to 450 nm, or 300 nm to 400 nm. Particles of CuO and cellulose acetate may be an average diameter of 20 nm to 200 μm, 25 nm to 180 μm, 50 nm to 150 μm, 75 nm to 125 μm, 100 nm to 100 μm, 200 nm to 10 μm, 500 nm to 1 μm, or 750 nm to 900 nm.

Figure 3B:
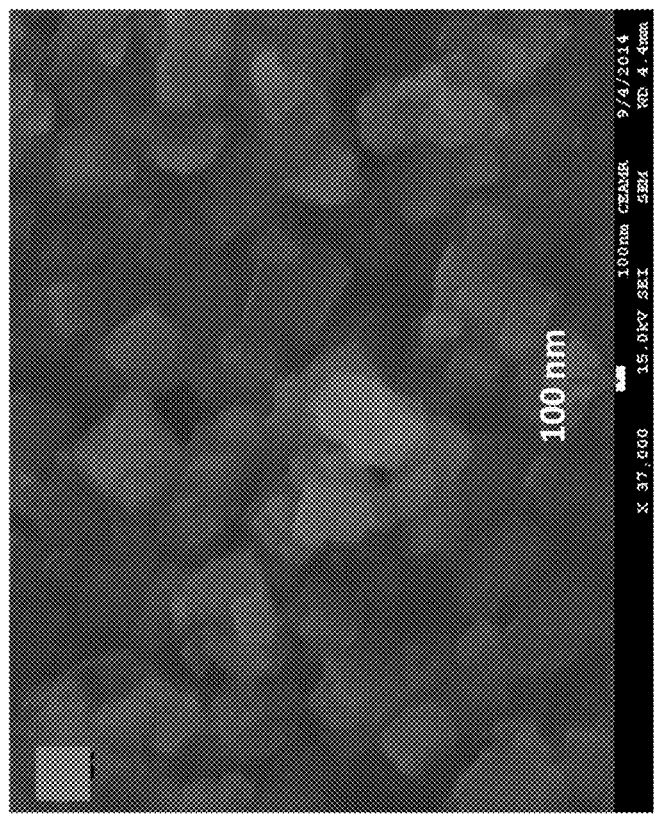
FIG. 3B is a FESEM image at 37000× of a surface of the resistance-based sensor in the cell configuration.
Figure 3A:
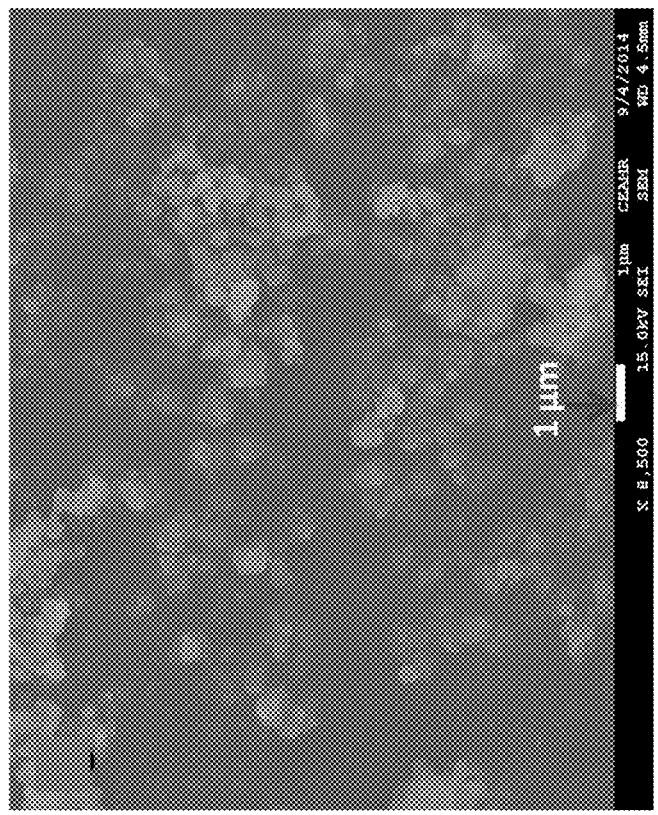
FIG. 3A is a FESEM image at 8500× of a surface of the resistance-based sensor in the cell configuration.

Exemplary images of the composite in the cell configuration, imaged at high magnification are shown in FIG. 3A and FIG. 3B. FIG. 3A is an exemplary section of the composite in the cell configuration at 8500× magnification and FIG. 3B is the same exemplary section of the composite in the cell configuration at 37000× magnification. In the cell configuration, the composite is relatively non-uniform, having a porosity of 0%-15%, 1%-12%, or 5%-10% relative to the whole surface area of the exemplary section and further, the pores are an average size of 0.01 nm to 500 nm, 0.1 nm to 400 nm, 1 nm to 300 nm, 10 nm to 200 nm, or 100 nm to 150 nm. Particles of CuO and cellulose acetate may be an average diameter of 20 nm to 200 μm, 25 nm to 180 μm, 50 nm to 150 μm, 75 nm to 125 μm, 100 nm to 100 μm, 200 nm to 10 μm, 500 nm to 1 μm, or 750 nm to 900 nm.

As described above, the porosity of the composite in the film configuration is greater than the porosity of the composite in the cell configuration, which may be a result of the pressure applied during the preparation of the composite in the cell configuration. Further, the higher porosity exhibited in the composite in the film configuration is beneficial for humidity sensing and may account for higher sensitivity of the humidity sensor due to the water molecules being able to passively diffuse into the pores, thus improving an electrical response. The composite in the film configuration may have a higher sensitivity than the composite in the cell configuration by 2% to 50%, 5% to 45%, 10% to 40%, or 20% to 35%.

In some embodiments, the exemplary particles may be cupric oxide particles held in cellulose acetate matrix. In some embodiments, the particles may be covered with cellulose acetate. In some embodiments, both cupric oxide particle and cellulose acetate may be mixed and are homogenously dispersed.

The electrodes employed in the resistance-based humidity sensor may comprise electrode materials that include, but are not limited to silver, gold, aluminum, or a combination thereof. The purpose of the electrodes in the humidity sensor as describe herein, is to connect the moisture sensitive composite to wires for metering devices, or environmental controls which are configured to read an electrical output from a resistance based humidity sensor as described herein. In some embodiments, the electrode may comprise a percentage of aluminum by weight relative to the total weight of the electrode in a range of 2% to 100%, 10% to 90%, 20% to 80%, or 40% to 60%. In some embodiments, the electrode may comprise a percentage of silver by weight relative to the total weight of the electrode in a range of 2% to 100%, 10% to 80%/a, or 20% to 60%, or 40% to 50%. In some embodiments, the electrode may comprise a percentage of gold by weight relative to the total weight of the electrode in a range of 1% to 100%, 10% to 90%, 20% to 80%, or 40% to 60%. The ratio by weight of aluminum to silver and/or gold may be in the range of 0:1 to 1:0, 1:3 to 4:1, 1:2 to 3:1, or 1:1 to 2:1. The ratio by weight of silver to gold may be 1:0 to 0:1, 1:3 to 4:1, 1:2 to 3:1, or 1:1 to 2:1.

Each electrode may be any shape sufficient to contact the composite and connect to a circuit or wiring. The electrode may have a total surface area of 2 mm² to 200 mm², 25 mm² to 150 mm², 50 mm² to 125 mm², or 75 mm² to 100 mm². In some embodiments of the sensor, more than two electrodes may be employed, but each electrode must be spaced a minimum of 30 micron apart, a minimum of 33 micron apart, a minimum of 35 micron apart, a minimum of 38 micron apart, or a minimum of 40 micron apart.

The sensitivity of the humidity sensor highly depends on a distance between the electrodes. The sensitivity of the presently disclosed sensor is defined as the ratio between the resistance and the relative humidity units (i.e. percent relative humidity). For example, the sensor measures relative humidity and has a change in voltage output as measured by resistance in MΩ, the sensitivity is a constant with the unit [MΩ/% relative humidity]. On increasing the distance between the electrodes a resistance measurement increases, while a capacitance measurement of the humidity sensor decreases. As the device's resistance (R) depends on geometrical parameters such as the distance between two electrodes (L) and cross-sectional area (A) and secondly on the resistivity (ρ) of the material which is an intrinsic property (i.e. a constant) of the material, the calculation can be expressed as shown in Expression (1).

$$R = \rho L/A \qquad \text{Expression (1):}$$

The dependence of the humidity sensor's capacitance (C) on the distance between two electrodes may be expressed by the following relationship Expression (2), where the distance between two electrodes is represented by (d), the dielectric constant is represented by (ε), and the cross-sectional area is represented by (A).

$$C = \varepsilon A/d \qquad \text{Expression (2):}$$

The distance or spacing between two electrodes affects performance of the sensor in terms of, but not limited to, sensitivity, sensing range and response time. The spacing between the electrodes of the present disclosure may be at least 30 micron, at least 40 micron, at least 50 micron, at least 60 micron, but no more than 70 micron.

An aspect of the present disclosure relates to employing the humidity sensor to measure a relative humidity of an environment, or an atmospheric measurement if outdoors. To take measurements of the relative humidity, the resistance-based humidity sensor may be connected to a circuit as exemplified in FIG. 1A and FIG. 1B. The circuit is depicted in FIG. 1A and FIG. 1B as a wire 105 connecting each electrode 102 to a meter 106. The term "wire" may include printed circuit boards, such as those included in process control devices. The meter 106 may be a voltimeter, multimeter, or the like. An exemplary process of measuring the relative humidity with the presently disclosed humidity sensor may be to apply a frequency by the meter into one side of the wire 105 connected to the first electrode. The frequency may be transmitted through the composite to the second electrode. The frequency may be carried through the wire 105 connecting the second electrode to the meter 106. The meter 106 may be connected with, or integrated with, a processor configured to correlate the changes in frequency (resulting from the changes in resistance of the composite) detected by the meter 106 to first a resistance of the composite and then to a relative humidity measurement. Frequency and resistance may be related by the capacitive-resistance formula in which R is the resistance, the f is frequency, and C is capacitance, and D is dissipation, each may be measured by standards familiar to people having ordinary skill in the art.

$$R = \frac{1}{2\pi fCD}$$

The relative humidity measurement calculated by the processor may be transmitted as a signal that may be displayed on an output device such as a monitor, screen, or LED display. In some embodiments the relative humidity measurement calculated by the processor may be transmitted to another device capable of regulating the relative humidity of an environment or an alert system to alert personnel to any change in the relative humidity of an environment.

In embodiments of the sensor when the composite is in the form of a film, as described herein, the resistance-based humidity sensor may be operated at an applied frequency in the range of 80 Hz to 120 Hz, 90 Hz to 110 Hz, 95 Hz to 100 Hz. At the applied frequency, the resistance-based humidity sensor has an initial average resistance in the range of 250 MΩ to 500 MΩ, 275 MΩ to 475 MΩ, 300 MΩ to 450 MΩ, 325 MΩ to 425 MΩ, or 350 MΩ to 400 MΩ. At the applied frequency, the resistance-based humidity sensor may exhibit an average capacitance in the range of 10 pF to 20 pF, 12 pF to 18 pF, or 14 pF to 16 pF. At the applied frequency, the resistance-based humidity sensor may exhibit an average change in resistance in the range of 2 MΩ per 1% relative humidity to 5 MΩ per 1% relative humidity, 2.5 MΩ per 1% relative humidity to 4.5 MΩ per 1% relative humidity, 3 MΩ per 1% relative humidity to 4 MΩ per 1% relative humidity. At the applied frequency, the resistance-based humidity sensor may exhibit an average change in capacitance in the range of 10 pF per 1% relative humidity to 25 pF per 1% relative humidity, 12 pF per 1% relative humidity to 24 pF per 1% relative humidity, 14 pF per 1% relative humidity to 22 pF per 1% relative humidity, or 16 pF per 1% relative humidity to 20 pF per 1% relative humidity.

In some embodiments of the resistance-based humidity sensor when in the form of a cell, as described herein, the resistance-based humidity sensor may be operated at and applied frequency in the range of 80 Hz to 120 Hz, 85 Hz to 115 Hz, 90 Hz to 110 Hz, or 95 Hz to 105 Hz. In the cell configuration and at the applied frequency, the resistance-base humidity sensor has an average resistance in the range of 15 MΩ to 40 MΩ, 20 MΩ to 35 MΩ, or 20 MΩ to 30 MΩ. The average change in resistance is in the range of 0.1 MΩ per 1% relative humidity to 1 MΩ per 1% relative humidity, 0.2 MΩ per 1% relative humidity to 0.8 MΩ per 1% relative humidity, or 0.5 MΩ per 1% relative humidity to 0.75 MΩ per 1% relative humidity.

The presently disclosed sensor may be further characterized by the response time and recovery time exhibited by the moisture sensitive composite. The response time is defined as the time required for the sensor output to change from a previous state to a final state. The previous state may be measured as the resistance of the sensor at a previous measurement time point, and the final state may be measured as the resistance of the sensor at a current time or any time point immediately after the previous measurement time point. The previous measurement point in time may be a time immediately prior to the current time in the range of 1 second to 120 seconds, 10 seconds to 100 seconds, 20 seconds to 60 seconds, or 40 seconds to 50 seconds. In some embodiments of the resistance-based humidity sensor, the sensor has a response time in the range of 8 seconds to 18 seconds, 10 seconds to 15 seconds, and 11 seconds to 13 seconds. The recovery time is defined as the time the sensor requires to return to a baseline value after being removed from the measured condition. The baseline value may be a measurement at 0% humidity or the baseline value may be averaged to be within 10% to 25%, or 15% to 20% of the measurement at 0% humidity. In some embodiments, the recovery time is in the range of 12 seconds to 22 seconds, 15 seconds to 20 seconds, or 17 seconds to 18 seconds.

Aspects of the present disclosure further relate to a method of producing a resistance-based humidity sensor. The method may include mixing copper(II) oxide and an alcohol forming a first mixture. The copper(II) oxide may be of a variety of forms, such as, but not limited to solid nanoparticles, nanopowders, nanotubes, nanoribbons, nanosheets, and combinations thereof. The alcohol into which the copper(II) oxide is mixed, may include methanol, ethanol, propanol, isopropanol and combinations thereof and the like, but other alcohols may also be used. Further, an azeotrope may be formed with the alcohol by including, ethyl acetate, methylacetate, ethyl formate, benzene, toluene, cyclohexane, ethyl nitrate, or acetonitrile. The cellulose acetate is mixed with the first mixture to form a second mixture. The cellulose acetate may be in the form of, but not limited to granules, flakes, sheets, or films. In some implementations, the granules, flakes, sheets, or films may be melted and reconstituted and/or powdered before mixing with the first mixture and forming the second mixture. The mixing may include sonication, grinding, blending, pressing, mechanical mixing via agitation by rotation of a paddle, propeller, or metal ribbon, pulsed-air mixing via jet mixer pumps, or by pulsed-liquid mixing via pulsed jet devices. In some implementations, during the mixing, heat may be applied at a temperature of 25° C. to 75° C., 30° C. to 70° C., 35° C. to 65° C., or 40° C. to 60° C. however, in some embodiments the mixing takes place at room temperature with no heat applied.

The electrodes employed in the humidity sensor may be attached to the inert substrate by an adhesive as described herein, or by integrating the electrodes into the inert substrate upon formation of the inert substrate. For example, in some implementations the inert substrate is a plastic and the electrodes may be molded into the plastic inert substrate. In some implementation the inert substrate may be a glass slide having a notched region on a surface of the glass slide which may incorporate an electrode to be flush with the surface of the glass slide. In some implementations, the electrode may be removable and or replaceable in the inert substrate. In implementations in which an adhesive is employed, the adhesive may be disposed on to the inert substrate by brushing, dipping, spraying, or extruding, such as from a tube. In some implementations, one electrode may be attached to the inert substrate, the composite film, or the cell then a cutting tool, such as a blade, laser cutting, or knife, may cut away a section of the one electrode to form two separate electrodes separated by a space. Employing a knife or cutting tool to cut one electrode into two electrodes after attaching the electrode to the inert substrate may be employed when the electrode comprises an aluminum foil, gold foil, or silver foil.

In some implementations there may be at least two electrodes, but less than 40 electrodes, less than 30 electrodes, less than 20 electrodes, less than 10 electrodes, or less than 8 electrodes employed in the humidity sensor. Each electrode may be spaced apart as described herein. In some implementations, each electrode may be independently connected with the circuit employed to measure the relative humidity.

Therefore, as used herein, the phrase "attaching at least two electrodes" may refer to the attachment of a plurality of pre-separated electrodes onto the inert substrate or the adhesive layer with a gap between each electrode, or alternatively to the attachment of a single electrode onto the inert substrate or the adhesive layer, followed by cutting or otherwise removing a portion(s) of the electrode to form at least two separated electrodes with a gap between.

The second mixture, as described, may be deposited onto at least a portion of the inert substrate or optionally the adhesive layer covering the portion of the substrate. The portion of the substrate is as described herein. The second mixture may be deposited onto the substrate by drop casting, injecting, spraying, dip coating, brushing, and spin-coating to uniformly cover the portion of the substrate. The second mixture contacts at least a portion of each of the electrodes. In some implementations, the electrodes may contact at least 5% to 100%, 10% to 90%, 20% to 80%, 30% to 70%, or 40% to 60% of the second mixture.

The second mixture may be dried onto the portion of the substrate or the adhesive layer in air or in a vacuum at a temperature of 25° C. to 55° C., 30° C. to 50° C., or about 35° C. to 45° C. The drying may continue for about 1 hour to 4 days or about 10 hour to 3.5 days, 1 day to 3 days, or 1.5 days to 2.5 days. In some implementations the drying may be accomplished at a ramped rate of heating, a rate of cooling, or both, of about 0.5° C./min to 3° C./min, about 0.75° C./min to 2.5° C./min, about 1° C./min to 2° C./min, or about 1.25° C./min to 1.5° C./min.

An aspect of the present disclosure further relates to a method of producing a resistance-based humidity sensor in the form of a cell. The method includes mixing copper(II) oxide and cellulose acetate without any additional solvents to form a mixture. The mixing may include, but is not limited to grinding and blending methods such as by a small scale mortar and pestle, industrial batch mixers, cone blenders, rotary glass batchers, and the like. After the mixing, the mixture may take the form of a blended powder. The powder may be of particle sizes in the range of 20 nm to 2 µm, 50 nm to 1.5 µm, 100 nm to 1 µm, 150 nm to 800 nm, 200 nm to 700 nm, 300 nm to 600 nm, 400 nm to 500 nm. The molding may be include pressing the mixture by a hydraulic press, mechanical press, or pneumatic press through a hollow mold to form a cell into shapes. The press may apply a pressure of 50 MPa to 2000 MPa, 100 MPa to 1500 MPa, 500 MPa to 1000 MPa, or 600 MPa to 800 MPa. In some implementations, the mixture is pressed into a mold of a shape such as a cube, cylinder, or other polygonic shape. In some implementations of the humidity sensor in the cell configuration, the electrodes may be attached to the composite on the same side or in the same plane, or exactly opposite sides of the cell in the same plane or in parallel planes. Electrodes may be attached to the cell spaced apart as described herein. In some implementations, the electrodes may be attached by adhesive to the cell as described herein.

In some implementations, the electrodes may be a liquefied metal paint which is painted onto the cell. The cell, with or without the electrodes, may be dried in ambient air pressure or in a vacuum at a temperature of 25° C. to 55° C., 30° C. to 50° C., or about 35° C. to 45° C. The drying may continue for about 1 hour to 4 days or about 10 hour to 3.5 days, 1 day to 3 days, or 1.5 days to 2.5 days. In some implementations the drying may be accomplished at a ramped rate of heating, a rate of cooling, or both, of about 0.5° C./min-3° C./min, about 0.75° C./min-2.5° C./min, about 1° C./min-2° C./min, or about 1.25° C./min-1.5° C./min.

The examples below are intended to further illustrate the humidity sensor and method of producing and are not intended to limit the scope of the claims.

EXAMPLE

Laboratory synthesized copper(II) oxide nanosheets of thickness 55-85 nm and commercially available cellulose acetate (Sigma Aldrich, USA) was used for the fabrication of humidity sensors. The CA-CuO nano-composites were prepared with a low temperature method, and mechanical mixing. By considering the nature of composite development techniques two types of sensors were fabricated: film and cell type sensors.

To fabricate the film sensors, the composite of cellulose acetate (CA) and copper(II) oxide (CuO) was prepared by a solution technique. In this technique the cellulose acetate and CuO nanosheets were mixed in 1.0 ml of ethanol. The CuO nanosheets were dispersed in the ethanol, while the CA was dissolved in the same (ethanol). The composite may be prepared in various ratios but the ratio employed in this example was 1:1 by weight (CA:CuO). The moisture sensitive composites may be fabricated without the use of elaborate chemical vapor, plasma enhanced or atomic layer deposition techniques. No major instruments are required to prepare the described humidity sensor.

A clean glass slide was employed as an inert substrate and an aluminum foil was used as an electrode. The foil was attached to the glass inert substrate by a double sided adhesive tape. As depicted in FIG. 1C, the glass slide 103 as represented in 111 is coated with an adhesive layer 104 as represented in 112. Aluminum foil as an electrode 102 is attached to the adhesive layer 104 as represented in 113. In this example, a knife was used to cut a space of 40 µm between the foil forming two electrodes. The size of each electrode was 5 mm in length and 5 mm in width. The mixture of the CuO and CA was placed upon the glass substrate and the electrodes by drop casting. The CA-CuO mixture was deposited by a syringe in 2 to 3 drops to form a 20 µm thick film over the electrodes and the substrate filling the space between the two electrodes. The composite 101 is deposited over and in the space between the electrodes 102 as represented in 114. After deposition the samples were kept at room temperature for 3 days to attain complete dryness.

The cell type sensors were fabricated by using the composite prepared by a mechanical mixing. In this example equal weights of CA and CuO powders were mixed homogenously by using a mortar and pestle. Cells of 10 mm diameter and 3 mm thickness were fabricated by pressing the mixed powder under the pressure of 1048 MPa by using hydraulic press. On the top of cell, the electric contacts (2×3 mm2) were made by using silver paste and there was a gap of 4 mm between the contacts (electrodes).

The testing of sensors was carried out at room temperature by using a simulated humidity setup in our laboratory. The simulation detail was replicated from Chani, M. T. S, et al. M. T. S. Chani, K. S. Karimov, F. A. Khalid, and S. A. Moiz, Solid State Sciences 18 (2013) 78, incorporated herein by reference in its entirety. The change in temperature and humidity inside the chamber was measured by digital humidity meter (Model 4085 Control Company, USA). The change in capacitance and dissipation of the sensor were measured by using LCR meter (Agilent U1733C). To calculate the resistance (R) following expression (3) was used:

$$R = 1/(2\pi fCD) \qquad \text{Expression (3)}$$

where f, C and D are frequency, capacitance and dissipation, respectively.

The surface morphologies of the CA-CuO composite films and cells were investigated by Field Emission Scanning Electron Microscope (FESEM) (FIG. 2A, FIG. 2B, FIG. 3A and FIG. 3B). FIG. 2A and FIG. 2B are the images of the surface morphology of films at low and high magnification, respectively, while FIG. 3A and FIG. 3B show the surface morphology for the cells. It can be seen in that the nanosheets are well dispersed in the cellulose acetate matrix, while the films have higher porosity as compared to cells. The reason for lower porosity in the cell's surface is the pressure applied during production of the cell. As higher porosity is favorable for humidity sensing, the surface with higher porosity may be expected to have higher sensitivity towards humidity. The porosity may support the water molecules diffusion, which improves humidity sensing (electrical response). EDS analysis of CA-CuO composite developed by solution and mechanical mixing techniques is shown in FIG. 4A, FIG. 4B, and FIG. 4C and FIG. 5A, FIG. 5B, and FIG. 5C, respectively. FIG. 4A and FIG. 5A are the FESEM images of the film and cell configurations of the moisture sensitive composite surfaces, respectively. FIG. 4B is a table of the weight percent and the atomic percentage of carbon 401, oxygen 402, and copper 403 on the surfaces measured from spectrum sample 400 in FIG. 4A. The analysis of the sample 400 is depicted in a spectrum in FIG. 4C. The presence of carbon, oxygen and copper(II) elements is confirmed by the analysis without any impurity. Similarly, FIG. 5B is a table of the weight percent and the atomic percentage of carbon 501, oxygen 502, and copper 503 on the surfaces measured from spectrum sample 500 in FIG. 5A. The analysis of the sample 500 is depicted in a spectrum in FIG. 5C. The presence of carbon, oxygen and copper(II) elements is similarly confirmed by the analysis without any impurity.

Figure 6:
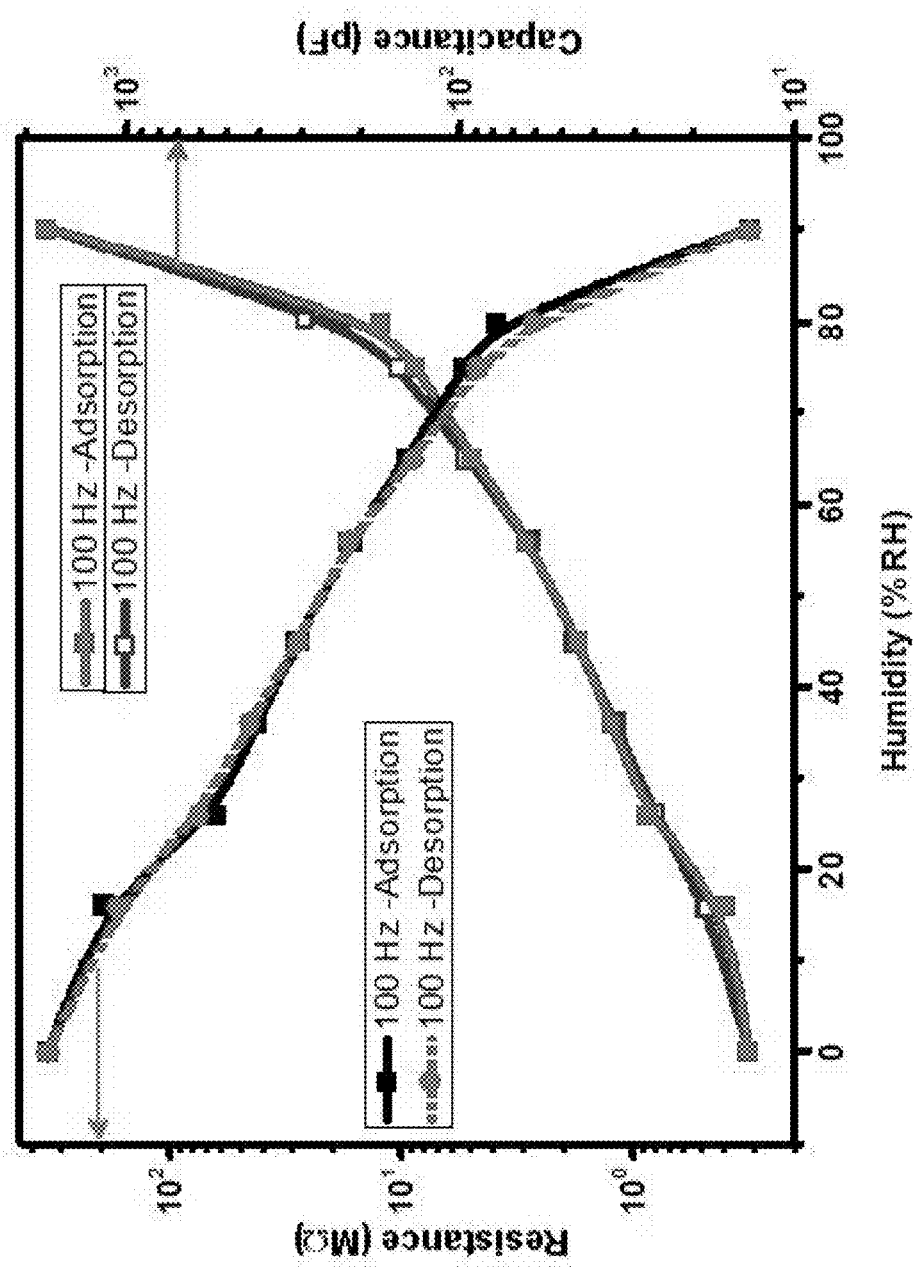
FIG. 6 is a plot of a capacitance and resistance-humidity relationships for the CA-CuO composite resistance-based humidity sensor in the film configuration.
Figure 7:
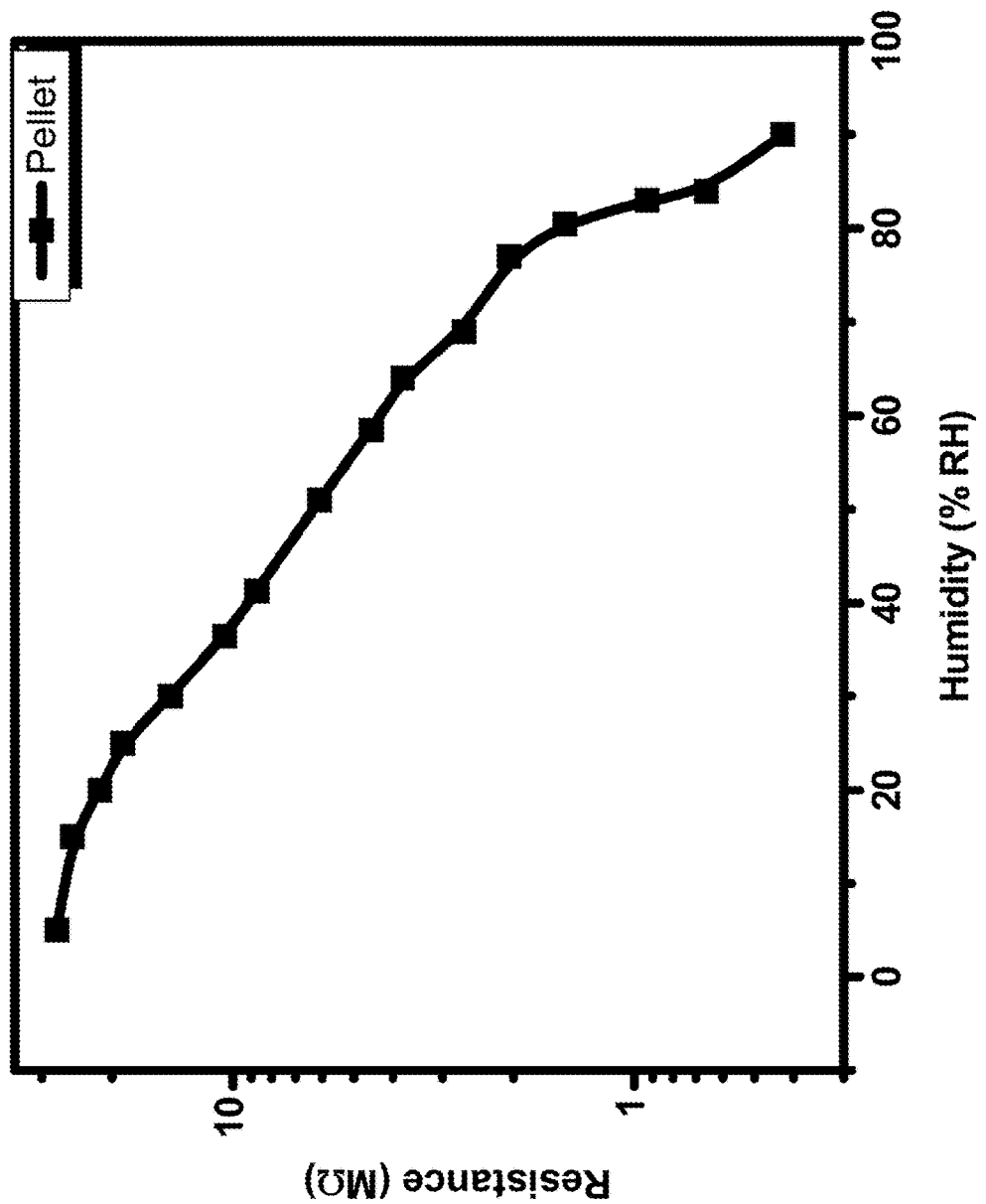
FIG. 7 is a plot of a resistance-humidity relationship for the CA-CuO composite resistance-based humidity sensor in the cell configuration.

FIG. 6 depicts a resistance-humidity and capacitance-humidity relationships on semi-logarithmic scale for the CA-CuO composite film based sensors. At a frequency of 100 Hz the initial average resistance and capacitance of the sensors are 338.7 MΩ and 13.7 pF, respectively, as depicted in FIG. 6. When the humidity changes from 0% to 90% RH, the resistance changes 1093 times, while change in capacitance is 127 times. The average change in resistance and capacitance is 3.8 MΩ/% RH and 19.2 pF/% RH, respectively. Change in resistance and capacitance with variation in humidity is quasi linear from 0% to 80% RH but when the humidity exceeded 80% RH the abrupt increase occurs in capacitance of the sensors, while the resistance decreases in a same fashion. This change in resistance and capacitance in response to change in humidity is attributed to water molecules absorption and adsorption (physisorption and chemisorptions) and secondly to the formation of charge transfer complexes. It is also evident from FIG. 6 that the sensors appear to exhibit a small hysteresis during adsorption-desorption process. The adsorption-desorption curves are well matched within the experimental error of ±2%. So there is no humidity memory effect or hysteresis which was previously observed in various polymeric materials. The reason for this behavior may be the high porosity and thinness of the composite films. The direct current resistance-humidity relationship for the cell type sensor is shown in FIG. 7. The initial resistance of the of the sensor is 27.5 MΩ and with change in humidity from 5 to 90% RH the resistance changes 67 times, while the average change in resistance is 0.27 MΩ/% RH. By comparing the resistance-humidity relationship graphs in FIG. 6 and FIG. 7 it can be seen that trend of both the graphs is the same.

Figure 8:
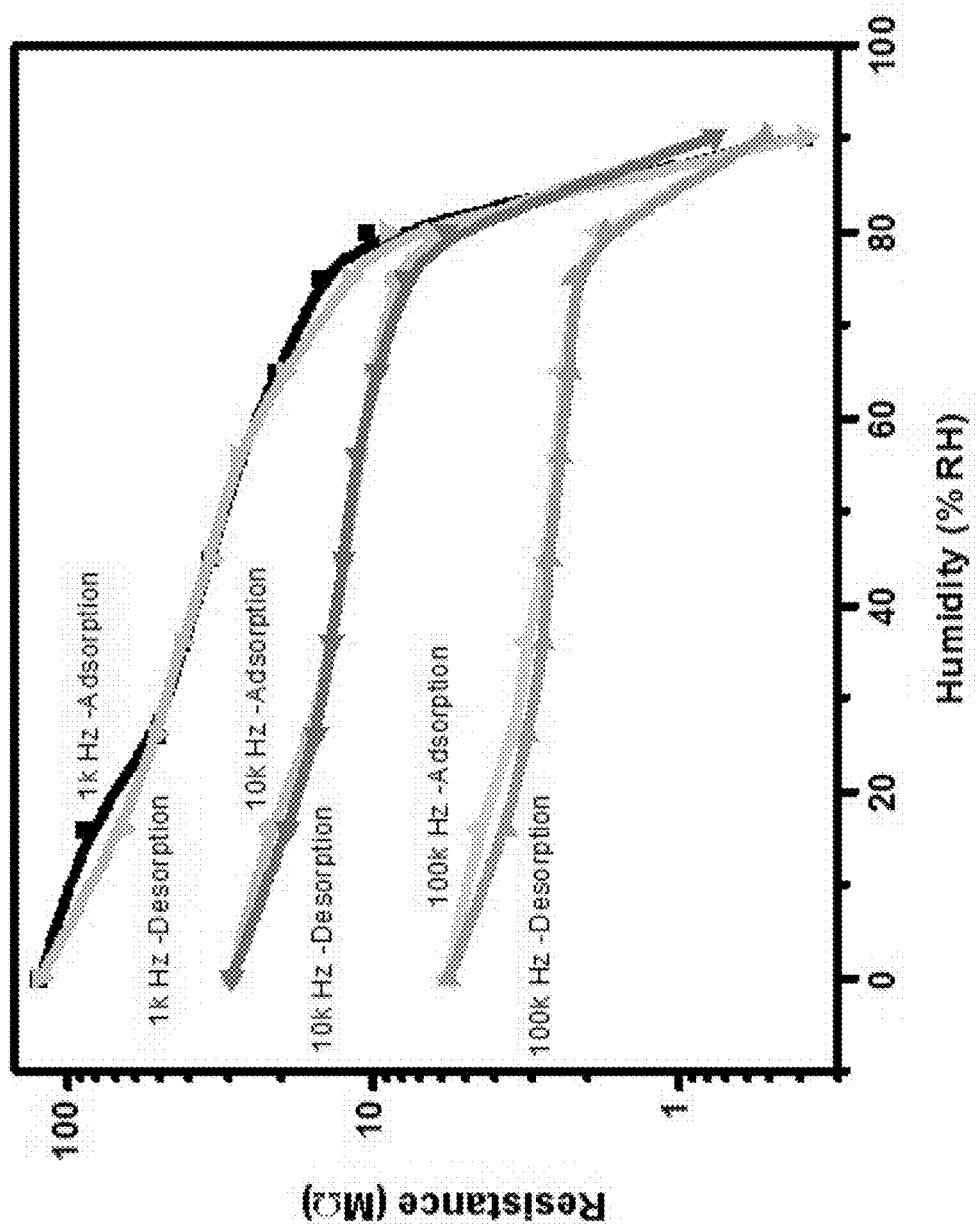
FIG. 8 is a plot of the effect of three frequencies on the resistance-humidity relationships of CA-CuO composite resistance-based humidity sensor in the film configuration.

The resistance-humidity relationships of the sensor at the frequencies of 1 to 100 kHz are also shown in FIG. 8, where it can be seen that upon increasing frequency the resistance of sensor decreases consistently with increase in humidity and this behavior can be observed throughout the sensing range. The reliance of resistance on frequency may be elucidated by the frequency dependency of dielectric permittivity, transit time of charges transfer and mobility of electrons and ions.

The sensing mechanism of the sensors may is based on variation of resistance and capacitance with humidity change. When the sensor is exposed to such environment where the humidity is very low but it increases gradually up to maximum; initially at lower humidity level the water vapors chemisorbed on the surface of the film or cell but on a further rise in humidity level the processes of physisorption takes place. The sensors show a change in resistance in the lower humidity range, but little change in capacitance. This change in resistance may be attributed to the electron donation to metal oxide by ionic conduction and chemisorption due to a minute absorption of water. On further increase in the humidity level the physisorption initiated and the condensation of water vapor starts on the surface and water molecules accumulate in layer by layer fashion. In the beginning of this stage the chemisorbed and first physisorbed layers take part in conduction by tunneling between donor $H_2O$ sites and electron hopping along the surface of the composite, while at the later stage the condensation results in protonic conduction, which decreases the rate of change of resistance. With the start of physisorption the rate of change of capacitance increases and it becomes stronger with increased condensation water layers. This change in capacitance is attributed to the high dielectric constant of water.

Other possible reasons for the decrease in resistance and increase in capacitance upon rise of humidity may include the doping of composite, absorption of water molecule in the composite, which may have augmented the capacitance and reduced the resistance due to a displacement current, and the formation of charge transfer complexes. Furthermore, there are several other factors that may affect the capacitance of sensor, which include the dielectric constant of active material (composite), area of electrodes and the gap between two electrodes. The capacitance also depends upon material's polarizability, based on the ionic ($\alpha_i$), electronic ($\alpha_e$) and dipolar ($\alpha_{dip}$) polarizability characteristic of the material. In normal conditions other source of polarizability may be the transfer of charge carriers (electrons and holes). Keeping in context of the sensor's response, it was assumed that the dipolar polarizability of the sensor increases by the absorption of water molecules in the composite layer.

Figure 9:
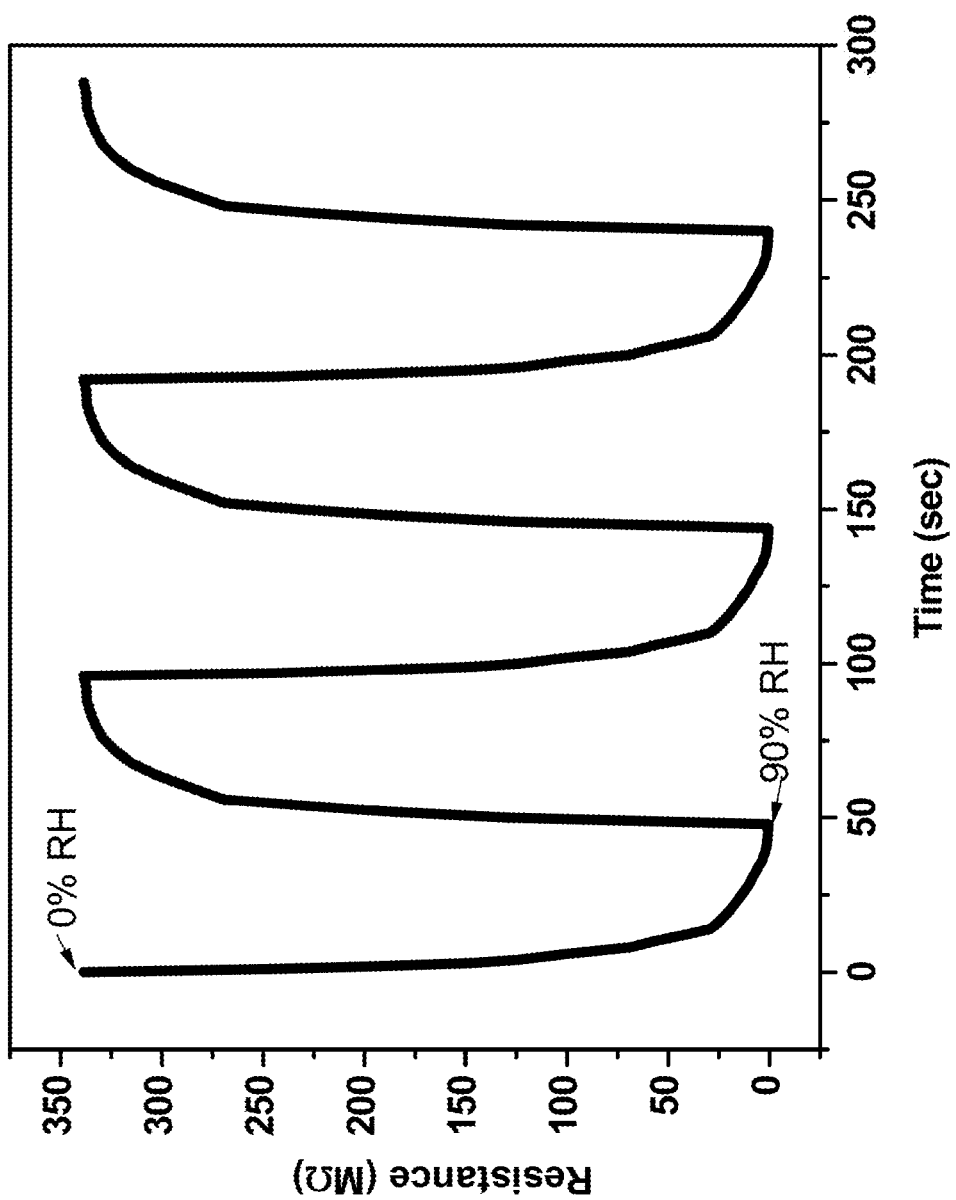
FIG. 9 is a plot of the response and recovery behavior of resistance-based humidity sensor in the film configuration.

The response and recovery times of the fabricated sensors were measured. The time required to measure 90% of the total change in the measuring electrical parameter of the sensor in response to the increasing and/or decreasing concentration or level of measured quantity or parameter is respectively called the response time ($\tau_{res}$) and the recovery time ($\tau_{rec}$). The response and recovery times are measured as 13 sec and 17 sec, respectively. FIG. 9 depicts the response and recovery behavior of the film based sensors at a frequency of 100 Hz.

The results of resistance-humidity relationships of the fabricated sensors (FIG. 6 and FIG. 7) have been simulated in the humidity range of 0 to 80% RH. For the simulation of experimental results the following exponential function was used:

$$f(x)=e^{-x}$$

The modified form of the above function for the simulation of resistance-humidity relationship of film sensor is the following:

$$R/R_o=e^{-k\Delta H(H+8H_m)/9H_m}$$

While for the humidity-resistance relationship of the cell type sensors the modified form of the above function is the following"

$$R/R_o=e^{-k\Delta H*3H/(2H+H_m)}$$

Where H is the instantaneous humidity, ΔH is the change in humidity (ΔH=H−H₀), $H_m$ is the maximum humidity, k is resistance-humidity factor, and R and $R_0$ are the resistances at instant and initial humidity levels, respectively. The resistant-humidity factor for film and cell type sensors is found as $5.6\times10^{-2}$ and $3.9\times10^{-2}$ respectively, accordingly for the 80% RH. The normalized experimental and simulated results of films and cell type sensors are shown in FIG. 10A and FIG. 10B, respectively. FIG. 10A and FIG. 10B depict the agreement between simulated results and experimental results.

As sensors have become extremely attractive for the scientists; a great variety of materials have been investigated for the development of humidity sensors. The comparison of methods used for the development of CuO based humidity sensors, their sensitivities and ranges has been given in Table 1. From Table 1 it can be seen that the CA-CuO based sensors fabricated by the present method without the use of instruments, have comparable or better sensitivity when compared to reported metal oxide based sensors.

TABLE 1

Comparison of method, range and sensitivity of the fabricated sensors with data present in literature for selected humidity sensors

| Sr.# | Sensing Material/Electrode | Fabrication Technique | Range (% RH) | Sensitivity |
|---|---|---|---|---|
| 1 | CuO, CuO-Silicone Adhesive | Thermal evaporation, Doctor blade technology | 38-90 | −2.9 to −4.8%/% RH |
| 2 | CuO nanoparticles | Pellets, Electron beam evaporation | 20-90 | 38 kΩ/% RH |
| 3 | CuO/CuS-Polymer | Pellets | 20-90 | −1.42%/% RH |

TABLE 1-continued

Comparison of method, range and sensitivity of the fabricated sensors
with data present in literature for selected humidity sensors

| Sr.# | Sensing Material/Electrode | Fabrication Technique | Range (% RH) | Sensitivity |
|---|---|---|---|---|
| 4 | KCl-doped Cu—Zn/CuO—ZnO | Screen printing | 11-95 | −1.2%/% RH |
| 5 | CuO/ZnO nanocorals | Hydrothermal growth and Spin coating | 30-90 | Sensitivity factor~6045 |
| 6 | Cellulose acetate-CuO | Instrument-less technique | 0-90 | 3.8 MΩ/% RH 19.2 pF/% RH |

Data Analysis

It was determined from the present analysis that the humidity sensitivity of the cellulose acetate-copper oxide nano-composite films based sensors of the example is 14 times higher than that of cell type sensors of the example. Due to compaction, the initial resistance of the cell type sensor is lower relative to the film type sensor. This compaction may result in reduction of porosity of the pellet, which in turn reduces the sensitivity of the pellet type sensors as compared to films based sensors that have comparatively higher porosity.

The invention claimed is:

1. A resistance-based humidity sensor comprising:
   a moisture sensitive composite comprising a cellulose acetate and copper(II) oxide; and
   a first electrode and a second electrode each in direct contact with the composite, wherein the first electrode and the second electrode are separated by the composite separated by the composite;
   wherein each electrode is connected to a circuit configured to correlate a resistance of the composite to a measurement of a relative humidity.

2. The resistance-based humidity sensor of claim 1, wherein a ratio of cellulose acetate to copper(II) oxide by weight is in a range of 1:4 to 4:1.

3. The resistance-based humidity sensor of claim 1, wherein the first and second electrodes are silver, gold, aluminum, or a combination thereof.

4. The resistance-based humidity sensor of claim 1, further comprising an inert substrate, wherein the moisture sensitive composite is on the inert substrate.

5. The resistance-based humidity sensor of claim 4, further comprising an adhesive layer between at least a portion of the moisture sensitive composite and the surface of the inert substrate.

6. The resistance-based humidity sensor of claim 4, wherein the inert substrate is nonporous.

7. The resistance-based humidity sensor of claim 4, wherein the composite is in the form of a film having a thickness in the range of 10 micron to 50 micron.

8. The resistance-based humidity sensor of claim 4, wherein at an applied frequency in the range of 80 Hz to 120 Hz, the resistance-based humidity sensor has an initial average resistance in the range of 250 MΩ to 500 MΩ, and an average capacitance in the range of 10 pF to 20 pF, and an average change in resistance is in the range of 2 MΩ to 5 MΩ per 1% relative humidity and an average change in capacitance in the range of 10 pF to 25 pF per 1% relative humidity.

9. The resistance-based humidity sensor of claim 1, wherein the composite is in the form of a cell having at least one dimension in the range of 2 mm to 10 mm.

10. The resistance-based humidity sensor of claim 9, wherein at an applied frequency in the range of 80 Hz to 120 Hz, the resistance-base humidity sensor has an average resistance in the range of 15 MΩ to 40 MΩ, and the average change in resistance is in the range of 0.1 MΩ to 1 MΩ per 1% relative humidity.

11. The resistance-based humidity sensor of claim 1, wherein the sensor has a response time in the range of 8 seconds to 18 seconds and a recovery time in the range of 12 seconds to 22 seconds.

12. A method of measuring a relative humidity in an environment with the resistance-based humidity sensor of claim 1, the method comprising:
    applying a frequency through the first electrode, across the moisture sensitive composite, and through a second electrode to measure a change in the frequency that correlates to a measurement of a resistance of the moisture sensitive composite and correlates to the relative humidity of the environment.

13. A method of producing a resistance-based humidity sensor, comprising:
    mixing a first mixture comprising copper(II) oxide and an alcohol with cellulose acetate to form a second mixture;
    attaching at least two electrodes to an inert substrate, such that the two electrodes are spaced apart by at least 30 microns;
    depositing the second mixture onto at least a portion of the inert substrate such that the mixture contacts at least a portion of each of the electrodes; and
    drying the second mixture.

14. The method of producing a resistance-based humidity sensor of claim 13, wherein a ratio of cellulose acetate to copper(II) oxide by weight is in the range of 1:4 to 4:1.

15. The method of producing a resistance-based humidity sensor of claim 13, wherein the electrodes are silver, gold, aluminum, or a combination thereof.

16. The method of producing a resistance-based humidity sensor of claim 13, wherein the inert substrate is nonporous.

17. A method of producing a resistance-based humidity sensor, comprising:
    mixing copper(II) oxide and cellulose acetate forming a mixture; molding the mixture into a cell and attaching at least two electrodes to the cell, spaced apart by 2 mm to 10 mm; and
    drying the cell.

18. The method of producing a resistance-based humidity sensor of claim 17, wherein a ratio of cellulose acetate to copper(II) oxide by weight is in the range of 1:4 to 4:1.

19. The method of producing a resistance-based humidity sensor of claim 17, wherein the electrodes are silver, gold, aluminum, or a combination thereof.

20. The method of producing a resistance-based humidity sensor of claim 17, wherein the molding comprises pressing the mixture through a hollow mold to form the cell.

* * * * *